United States Patent [19]

Mixich et al.

[11] 4,443,612
[45] Apr. 17, 1984

[54] PROCESS FOR THE STEREOSPECIFIC PREPARATION OF IMIDAZOLYL OXIMES

[75] Inventors: Georg Mixich; Kurt Thiele, both of Zofingen, Switzerland

[73] Assignee: Siegfried Aktiengesellschaft, Zofingen, Switzerland

[21] Appl. No.: 412,943

[22] Filed: Aug. 30, 1982

Related U.S. Application Data

[63] Continuation of Ser. No. 211,172, Nov. 28, 1980, abandoned, which is a continuation-in-part of Ser. No. 40,425, May 18, 1979, abandoned.

[30] Foreign Application Priority Data

May 24, 1978 [CH]  Switzerland .................... 5653/78
Jan. 9, 1979 [CH]  Switzerland ...................... 161/79

[51] Int. Cl.³ .......................................... C07D 233/61
[52] U.S. Cl. .................................................... 548/341
[58] Field of Search ........................................ 548/341

[56] References Cited

U.S. PATENT DOCUMENTS

| | | | |
|---|---|---|---|
| 2,880,238 | 3/1959 | Kundiger et al. | 564/256 |
| 3,236,889 | 2/1966 | Pawloski | 564/256 |
| 3,441,608 | 4/1969 | Schutz et al. | 564/257 |
| 3,903,164 | 9/1975 | Goransson-Dahlander | 564/257 |
| 4,038,317 | 7/1977 | Wermuth et al. | 564/256 |
| 4,124,767 | 11/1978 | Mixich et al. | 548/341 X |

Primary Examiner—Richard A. Schwartz
Attorney, Agent, or Firm—Burns, Doane, Swecker & Mathis

[57] ABSTRACT

1-Aryl-2-(1H-imidazol-1-yl)-ethanone oxime ethers are known to exist as a mixture of isomers corresponding to the formulae:

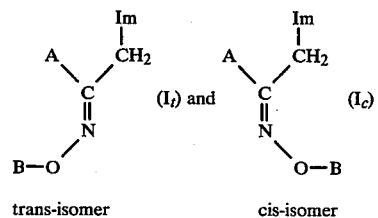

trans-isomer         cis-isomer

To prepare such an isomer in a stereospecifically pure form, the pure stereoisomer of the corresponding ethanone oxime is first converted into an alkali salt in a polar solvent, such as acetone or dimethylformamide, using an alkali in an amount somewhat less than the equimolar amount with respect to the said ethanone oxime, and is then converted to the desired ether by reacting it at a temperature not higher than 40° C. with a halogen compound capable of forming the desired ether. Isolation of the ether product is obtained as the free base or by precipitating it as an acid addition salt upon addition of a suitable organic or mineral acid, preferably nitric acid. A stereospecific ethanone oxime in either its trans- or cis-isomer form corresponding to the formula:

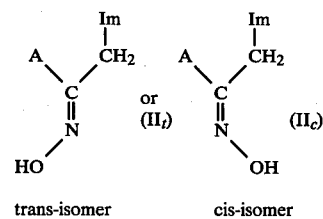

trans-isomer         cis-isomer can be stereospecifically synthesized from the corresponding 2-halogen ethanone having the formula A—CO—CH₂—Hal (IV) which, in making the cis oxime (IIc), is first converted with imidazole or a suitably substituted derivative thereof and subsequently oximated by reaction with hydroxylamine in the presence of a molar excess of an alkali at an elevated temperature; or which, in preparing the trans oxime (IIt), is first oximated by reaction with hydroxyl-amine under mild conditions and subsequently converted in the cold with imidazole or a suitably substituted derivative thereof. The products are effective fungicides or bactericides and consequently useful as thermotherapeutic agents in combatting undesirable lower plant organisms in the fields of human as well as veterinary medicine and also as fungicides in agriculture and horticulture.

1 Claim, No Drawings

PROCESS FOR THE STEREOSPECIFIC PREPARATION OF IMIDAZOLYL OXIMES

CROSS-REFERENCE TO EARLIER APPLICATIONS

This application is a continuation of U.S. application Ser. No. 211,172 filed Nov. 28, 1980, now abandoned, which is a continuation-in-part of U.S. application Ser. No. 40,425 filed May 18, 1979 and now abandoned.

SUMMARY OF THE INVENTION

The invention concerns a process for the stereospecific preparation of imidazolyl oxime ethers having the formula:

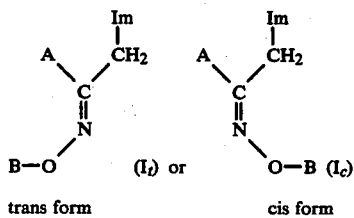

wherein
A signifies a carbocyclic aromatic or thienyl or pyridyl radical containing 1 or 2 nuclei, wherein each nucleus contains from zero to two substituents selected from the class consisting of halogeno, alkyl and alkoxy containing 1 to 4 carbon atoms, cycloalkyl radicals containing 3 to 6 carbon atoms per nucleus, phenyl, and nitro and amino groups, and wherein said cycloalkyl and phenyl in turn may contain the same or different substituents from the same described class as the said aromatic radical first named above, B signifies a member of the group consisting of saturated and unsaturated aliphatic radicals of 1 to 8 carbon atoms, saturated and unsaturated aliphatic radicals of 1 to 8 carbon atoms containing one or two substituents of the class defined above for A, which substituents are bound directly or via an oxygen atom to the aliphatic radical, cycloaliphatic radicals of 3 to 6 carbon atoms, and cycloaliphatic radicals of 3 to 6 carbon atoms containing up to three substituents selected from the class consisting of halogeno, nitro groups and alkyl and alkoxy groups of from 1 to 4 alkyl carbon atoms, and Im signifies a 1-H-imidazol-1-yl group that is substituted with zero to two substituents selected from the class consisting of halogeno, alkyl and alkoxy of from 1 to 4 alkyl carbon atoms, and not more than one nitro group.

The process comprises the conversion of the correspondingly substituted pure stereoisomer oxime compound having the formula:

in which Im and A have the meanings given above, to a metal oximate by adding to the resulting mixture at about room temperature an amount of a basic metal compound capable of forming a metal oximate with said oxime isomer, said amount being somewhat less, preferably about 5 to 15 mole % less than the equimolar amount of said basic metal compound relative to said oxime isomer of formula (II), and reacting the metal oximate thus obtained with a compound of the formula

X—B     (III)

in which B has the meaning given above and X is a sulfonic acid ester radical or preferably a halogen atom, most preferably chlorine or bromine, and which compound is capable of forming an ether compound with the oxime. Compounds wherein B is an unsubstituted or, more especially, a halogen substituted benzyl radical are particularly preferred at this time.

The invention also relates to a process for the preparation of the pure stereoisomer oximes themselves from which the ethers of the formulae (I$_t$) and (I$_c$) are obtained, namely a process for the stereospecific preparation of imidazolyl oxime compounds of the formula:

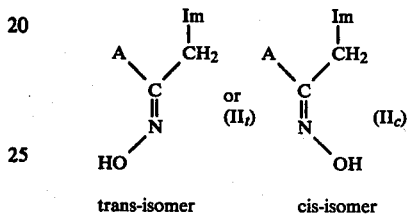

wherein A and Im have the meaning given above.

Within the framework of the disclosed invention the terms "trans" and "cis" have significance illustrated by the disclosed chemical formulae (I$_t$) and (I$_c$) or (II$_t$) and (II$_c$). In the E/Z system (C.A. Service, 1968, Blackwood et al and IUPAC Tentative Rules for the Nomenclature of Organic Chemistry) the "trans form" defined by the formula (I$_t$) or (II$_t$) corresponds to the E isomer when the radical A is a substituted phenyl radical whereas the "cis form" of the formula (I$_c$) or (II$_c$) corresponds to the Z isomer under these conditions.

PRIOR ART

Imidazolyl oxime compounds of the formula (II) and imidazolyl oxime ether derivatives prepared from them are disclosed in DE-A No. 26 57 578 and corresponding U.S. Pat. No. 4,124,767. This reference also specifically discloses that one of the two possible stereoisomeric oximes is formed when 2,4-dichlorophenacyl imidazole is oximated in the laboratory with hydroxylammonium chloride in ethanol in the presence of pyridine, whereas in the absence of pyridine the other one of the two stereoisomeric oximes is formed under otherwise identical conditions. Relatively pure 1-(2,4-dichlorophenyl)-2-(1H-imidazol-1-yl)-ethanone oximes were thus obtained. A stereochemical assignement of the compounds did not occur.

However, further work along these lines has surprisingly shown that the specific reactions previously disclosed are not sufficiently reproducible when scaled up to a commercial scale and, moreover, are not applicable to the conversion of analogous compounds. In attempting to carry out such a stereospecific synthesis on a commercial scale, or to apply it to analogous reactions, isomeric mixtures rather than the pure isomers were obtained. Further tests did show that this also is true when carrying out the known process in the laboratory scale, regardless of the presence or absence of pyridine. Upon recrystallization of the isomeric mixtures the less soluble cis-oxime in fact is obtainable therefrom, but the yield is poor.

The 1-(2,4-dichlorophenyl)-2-(1H-imidazol-1-yl)-ethanone oximes described in DE-OS No. 26 57 578 and U.S. Pat. No. 4,124,767 were also disclosed there to have been etherified in dimethylformamide in the presence of an equimolar amount of sodium hydride, based on the oxime, at a temperature gradually increasing from room temperature to 80° C. In this etherification the stereoisomers of 1-(2,4-dichlorophenyl)-2-(1H-imidazol-1-yl)-ethanone oxime-(2,4-dichlorobenzyl) ethers are likewise alleged to have been obtained without stereochemical rearrangement.

However, subsequent work along these lines has likewise shown that the etherification disclosed in the prior art definitely does not proceed stereospecifically when it is scaled up to a commercial scale. The NMR-spectra clearly show that under commercial-scale conditions substantial amounts of the other unwanted stereoisomer are also obtained in the commercial product although a sterically pure isomer can be obtained after separation and purification when working on a small scale. The reproducibility and the yield (21%) of said known process are poor.

Of course, it is desirable to produce the imidazolyl oxime and oxime ether compounds in a stereochemically pure form on a large scale, because of their generally high antimycotic activity. While preparation of such pure isomers is readily achievable in the laboratory, for instance by chromatographic separation, such chromatographic separation is not economical on a commercial scale.

OBJECTS OF THE INVENTION

It is therefore an object of this invention to provide a commercially practical process for the stereospecific preparation of imidazolyl oxime ether and imidazolyl oxime compounds corresponding to the formulae ($I_t$) or ($I_c$) and ($II_t$) or ($II_c$) described above.

More particularly, it is an object to provide such a process that is capable of yielding the desired pure stereoisomer in a dependable and reproducible manner and in acceptable yields regardless of the scale of operation and that is effective for the production of a wide variety of specific imidazolyl oxime and oxime ether compounds.

GENERAL DESCRIPTION

According to this invention such production is achieved by suspending or dissolving an oxime compound of formula (II) in the form of the proper and pure stereoisomer

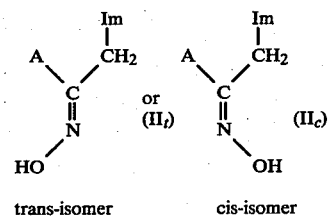

trans-isomer      cis-isomer at room temperature in a polar organic solvent, subsequently treating it at room temperature with a metal compound capable of forming a metal oximate, and then carrying out the etherification by adding to the resulting solution a halogen compound of the formula (III) disclosed above and maintaining the temperature of the reaction mixture at or below 40° C.

In the above step of forming the metal oximate or either the trans-oxime or the cis-oxime it is one of the most important features of the invention that the basic metal compound used for forming the metal oximate shall be present in the reaction system only in an amount which is somewhat less, preferably about 5 to 15 mole % less than the equimolar amount of said metal compound relative to said oxime-isomer of ether formula ($II_t$) or ($II_c$). If the metal compound is present in an amount equal to or greater than said equimolar amount, then an isomerization will occur and the obtainable product is but a mixture of the two stereoisomeric ethers of formulae ($I_t$) and ($I_c$) rather than a stereochemically pure compound of either formula ($I_t$) or formula ($I_c$).

For achieving the objects of the invention it is a further essential feature of the invention that the oxime compound of formula (II) is provided as a pure substance in either of its stereoisomeric forms when carrying out the above etherification reaction. For producing said stereoisomers, regardless of whether the trans oxime corresponding to the formula ($II_t$) or the cis oxime corresponding to the formula ($II_c$) is to be prepared, one starts with the corresponding 2-halogen ethanone of the formula

wherein A has the meaning given in the Summary above and Hal is a halogen atom, e.g., chlorine, bromine, iodine or fluorine.

However, in preparing the cis oxime ($II_c$) the ethanone (IV) is first reacted with imidazole or an imidazole compound having the desired substituents so as to produce the corresponding 2-(imidazol-1-yl) compound and the latter is subsequently heated in methanol, ethanol or similar alcoholic solution in the presence of a molar excess of an alkali with hydroxylamine of a hydroxylamine compound that liberates hydroxylamine under the reaction conditions, thereby producing the desired cis-oxime product ($II_c$). As free hydroxylamine is relatively unstable, it is generally preferable to use acid salts thereof such as hydroxylammonium sulfate, sodium hydroxylamine mono- or disulfonate or the like as a source for the required hydroxylamine.

It is a further important feature of the invention that the above cis-oximation is carried out in the presence of an alkali in an amount corresponding to a substantial molar excess, preferably to at least double the equimolar amount, for example from about two times to about eight times the equimolar amount relative to said hydroxylamine and hydroxylamine-yielding compound, respectively. This condition shall include as a matter of fact the understanding that the amount of the alkali simultaneously shall correspond to a molar excess relative to said 2-(imidazol-1-yl)-ethan-1-on derivative. When carrying out the oximation of the imidazolyl substituted ethanone derivative in the absence of said molar excess of an alkali, isomerization will take place and a mixture of the corresponding cis and trans oximes is obtained instead of a stereochemically pure cis-oxime.

By contrast, in preparing the trans oxime ($II_t$), the ethanone (IV) is first converted to a 2-halogen-cis-oxime of the formula

by treatment with hydroxylamine or a hydroxylamine yielding hydroxylamine compound in an alcohol solution at a temperature not substantially above room temperature, e.g., below 35° C., preferably between 0° and 25° C., and the halogen-cis-oxime is then converted to the trans oxime ($II_t$) by reaction with imidazole or a corresponding imidazole derivative in an aprotic solvent in the cold wherein a cis-trans rearrangement occurs. In this reaction the cis-oxime of formula ($V_c$) is easily obtained due to the absence of the imidazolyl substituent. If the imidazolyl substituent already were introduced before the oximation step, the above described isomerization would take place yielding a mixture of the corresponding cis and trans oximes rather than a stereoisomerically pure product.

Either of the stereoisomeric imidazolyl oxime compounds ($II_t$) and ($II_c$), which themselves have antimycotic and bactericidal activity and are therefore valuable, thus is prepared according to this invention from the corresponding 2-halogen ethanone of the formula A—CO—CH$_2$—Hal (IV), in which A has the meaning given above and Hal is a halogen atom, e.g., chlorine, bromine, iodine or fluorine. However, when preparing a cis oxime ($II_c$), the ethanone of formula (IV) is first reacted with imidazole or a suitably substituted imidazole compound to produce the corresponding 2-(imidazol-1-yl) compound and the latter is thereafter reacted in the presence of a molar excess of an alkali in an alcoholic solution while heating with hydroxylamine or a hydroxylamine derivative that yields hydroxylamine under the reaction conditions, thereby preoducing the desired cis oxime ($II_c$). On the other hand, when preparing the trans oximes ($II_t$) the ethanone (IV) is first converted to a 2-halogen-cis-oxime of the formula

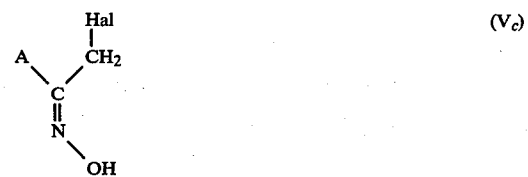

by reaction with hydroxylamine or a hydroxylamine yielding derivative of hydroxylamine at a temperature not substantially above room temperature and then converted to the trans oxime ($II_t$) by reaction with imidazole or a suitably substituted imidazole compound in an aprotic solvent in the cold wherein a complete cis-trans rearrangement occurs. This imidazolation of the 2-halogen cis oxime ($V_c$) that takes place with said cis-trans rearrangement is preferably carried out in an apolar aprotic solvent, e.g., chloroform, at a temperature in the range of from 0° to 5° C. Other suitable aprotic solvents include methylene chloride, and many others, as is well known in the art.

In the single known case mentioned earlier herein of a reported preparation of the stereoisomeric imidazolyl oxime ether compounds of formulae ($I_t$) and ($I_c$), the etherification that was reportedly essentially stereospecific when conducted on a small scale has thus far not been successfully translated into a commercial-scale process in a sufficiently reproducible manner, nor has it been found practical for the preparation of other, analogous compounds, nor has it been found to be even safely reproducible on a laboratory scale. The reason for such failure, as now has been revealed, is in the known process the use of an equimolar amount of alkali rather than a sub-equimolar amount. It has been found that surprisingly the presence of an alkali in an amount of equal to or greater than the equimolar amount relative to said oxime compound has a catalytic effect on the isomerization reaction.

However, isomerization during the etherification can be completely excluded in the presence of a sub-equimolar amount of an alkali. The invention thus provides a secure, reproducible, practical, commercial-scale process for the stereoselective and stereospecific preparation of all the cis or trans isomers or the E/Z isomers of imidazolyl oxime ether compounds of the class described.

The same is also true with respect to the stereospecific and stereoselective preparation of the imidazolyl ethanone oxime compounds ($II_t$) or ($II_c$), respectively, which are required as intermediates in the preparation of the oxime ethers but which themselves also constitute valuable end products. More particularly, when preparing the cis oxime ($II_c$) according to this invention, the corresponding 2-halogen ethanone (IV) is first imidazolated and only then oximated in the presence of a molar excess of an alkali, whereas, conversely, when preparing the trans oxime ($II_t$) the 2-halogen ethanone (IV) is first oximated, i.e., oximated to the 2-halogen-cis oxime of formula ($V_c$), and the latter is then converted and rearranged to the trans form in the subsequent imidazolation (ch. J. Amer. Chem. Soc. 94, 9274-77).

The stereoisomeric oximes ($II_t$) and ($II_c$) show different melting points and a different chromatographic behaviour, especially clearly different RF values in a thin-layer chromatogram, and can in every case be clearly identified as one or the other of the stereoisomeric forms on the basis of their NMR-spectroscopic data.

The stereoisomeric imidazolyl oxime ether compounds ($I_t$) and ($I_c$) also exhibit different melting points, a distinctly different chromatographic behaviour, likewise particularly RF values that are clearly different in a thin-layer chromatogram. The products can clearly be identified from the NMR spectrum as the cis form or trans form, i.e., the (E) form or the (Z) form. This identification of a product as one or the other isomer is also particularly possible because of the displacement of the CH$_2$ protons ($\delta_{cis} > \delta_{trans}$).

According to a further development of this invention the stereospecific etherification for the preparation of the cis isomer ($I_c$) is preferably carried out in a lower ketone solvent such as acetone in combination with an alkali metal hydroxide, e.g., KOH or NaOH, the quantity of hydroxide added being somewhat smaller than equimolar, preferably about 5 to 15 mol percent smaller than the equimolar amount of hydroxide relative to the oxime. On the other hand when preparing the trans isomer ($I_t$) one works preferably in dimethylformamide in combination with an alkali metal hydride, e.g., NaH, LiH or KH. Also in the latter case, i.e. when preparing the trans isomer ($I_t$), the quantity of the alkali added, preferably the alkali metal hydride added, is somewhat smaller than equimolar, preferably about 5 to 15 mol % smaller than the equimolar amount of the alkali relative to the oxime.

In both cases, i.e. when preparing the cis-ether and when preparing the trans-ether of the formulae ($I_c$) and ($I_t$), respectively, the imidazolyl oxime ether compound so prepared is preferably isolated from the reaction mixture as an acid addition salt upon addition of a suitable organic or mineral acid, e.g., aqueous hydrochloric, sulfuric, phosphoric, nitric, acetic, citric, tartaric, malonic, maleic, fumaric, succinic, salicyclic, lactic, glycolic, benzoic, para-aminobenzoic, methanesulphonic or cyclohexylsulfaminic acid. Aqueous nitric acid is generally preferred, although any other salt forming acid that is teleologically acceptable, i.e., acceptable for the particular intended end use of the product, e.g., as a fungicide or bactericide, can be used similarly. Obviously, for instance, when the product is to be applied as a fungicide or bactericide to an animal or to an agricultural crop which is to be rid of a fungus or bacteria, the selected acid should be one that is not unduly injurious to the animal or the crop.

The stereoisomerically pure imidazolyl ethanone oxime compounds ($II_t$) and ($II_c$), which are required as intermediates, are prepared as described above. In any case, the recovery of the respective individual stereoisomer in a form substantially free from its other stereoisomer is desirable not only when it is used as an intermediate in the synthesis of more complex stereoisomeric derivatives thereof but when it is used as a biological agent having biocidal properties that are specifically different from those of its other stereoisomer.

The process of the invention is particularly distinguished by its dependability and its applicability to the entire class of compounds defined by formulae I and II. Of particular interest at this time, however, are those compounds within this class wherein the radicals A, B and Im in formulae I and II, or in formulae I to V, have the significance specified immediately herein below. More particularly, the invention preferably used for the preparation of compounds wherein: (1) the radical A is an unsubstituted or once or twice substituted phenyl radical or a phenyl radical containing 1 to 2 substituents selected from the class first defined above in the Summary portion of this specification, preferably one or two halogen atoms, such as chlorine, bromine, iodine or fluorine, most preferably chlorine; (2) the radical B is a phenylalkyl radical of 1 to 4 carbon atoms in the alkyl portion, preferably a benzyl radical, which contains from 0 to 3 substituents in the benzene ring the substituents being selected from the class first defined above in the Summary portion of this specification, preferably halogen atoms, such as chlorine, bromine, iodine or fluorine, most preferably chlorine atoms; and (3) Im signifies an unsubstituted 1H-imidazol-1-yl radical.

The greatest value of the invention is currently believed to reside in the fact that even those compounds corresponding to formulae I or II can be conveniently prepared in a stereochemically pure form on a commercial scale in which (1) the radical A is a 4-chlorophenyl or a 2,4-dichlorophenyl radical; (2) the radical B is a 4-chlorobenzyl or 2,4-dichlorobenzyl; and (3) Im is an unsubstituted 1H-imidazol-1-yl radical.

Other stereochemically pure isomers corresponding to formulae I or II which are most readily prepared in accordance with this invention include compounds wherein the radical A is an unsubstituted phenyl or naphthyl, or 4-bromo- or 2,4-bromo- or 4-fluoro- or 4-iodophenyl.

SPECIFIC EMBODIMENTS

The invention is further illustrated by the following working examples.

EXAMPLE 1

(Z)-1-(2,4-Dichlorophenyl)-2-(1H-imidazol-1-yl)-ethanone oxime

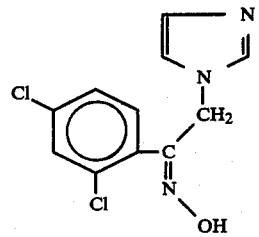

1205 g (5.4 moles) 2,4-dichlorophenacyl chloride is dissolved in 1800 ml dichloromethane and the solution is then added dropwise within a time of about 6 hours to a suspension of 1101 g (16.2 moles) imidazole in 5500 ml dichloromethane while vigorously stirring and maintaining the temperature of the reaction mixture at about 0° C. to 5° C. Thereafter the mixture is continually stirred at this temperature for 1 hour. Stirring then is continued for about 16 hours at room temperature. The solvent then is distilled off in a vacuum evaporator keeping the temperature of the reaction mixture below 40° C. The residue is poured into 6 l water, and the obtained mixture is vigorously stirred, whereupon the reaction product is precipitated. The reaction product is filtered off and washed with water. The raw product thus obtained in a yield of 90% can be directly oximated without any further purification.

1240 g (4.9 moles) of the thus prepared 2,4-dichlorophenacyl-1H-imidazol is dissolved in 6.2 l methanol. 506.6 g (7.3 moles) hydroxylammonium chloride and 818.2 g KOH (14.6 moles) are added to this solution, which then is heated for one hour under reflux while stirring. After cooling the reaction mixture is poured into 5330 ml aqueous HCl having a concentration of 5% by weight, whereby the oxime product is precipitated. About one hour later the solid product is filtered off and well washed with water. Then after well drying the thus obtained raw product is recrystallized from ethylene glycol monomethyl ether. The pure oxime product, i.e. the (Z)-1-(2,4-dichlorophenyl)-2-(1H-imidazol-1-yl)-ethanone oxime thus is obtained in the form of colourless crystals having a melting point of 227°–229° C. The yield is 89%. The purity and the identity of the obtained product were confirmed by chemical analysis, TLC, NMR and IR absorption spectra.

EXAMPLE 2

(Z)-1-(2,4-Dichlorophenyl)-2-(1H-imidazol-1-yl)-O-(2,4-dichlorobenzyl-ethanone oxime nitrate

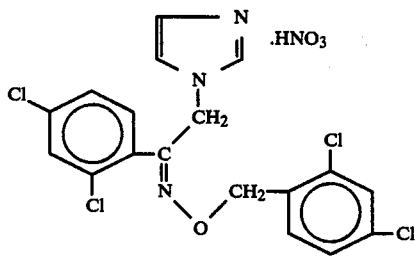

2064 g (7.64 moles) (Z)-1-(2,4-dichlorophenyl)-2-(1H-imidazol-1-yl) ethanone oxime as obtained in Example 1 is suspended in five times its amount (10.3 l) acetone, vigorously agitated and 386 g KOH (6.88 moles) is added to the suspension in the form of a fine powder. The suspended ethanone oxime is thus gradually dissolved. After about one hour 1554 g (7.9 moles) 2,4-dichlorobenzyl chloride is added to the solution in a single portion. The resulting reaction is slightly exothermic and causes the temperature of the reaction mixture to rise to between 35° and not more than 40° C. In order to complete the reaction the reaction mixture is agitated for 4 additional hours while maintaining the temperature of the reaction at not more than 40° C., with some slight cooling if necessary. Upon completion of the reaction the mixture is poured into 15 l water. Thereafter the product of the reaction is precipitated as the nitrate by adding 6 l of aqueous 2n HNO₃.

A few hours after precipitation of the nitrate the mixture is filtered and the precipitate throughly washed with water. The thus separated raw nitrate is recrystallized in 11.3 l of 94% ethanol. A second recrystallization in 3 times the stated amount of ethanol yields the final product in the form of colorless crystals having a purity of 99.95%. The purity of the obtained product is checked by thermal analysis. The melting point of the resulting crystals is between 139.5° and 140.5° C. The yield obtained was 62.5%.

Elemental analysis for $C_{18}H_{13}Cl_4N_3O \cdot HNO_3$ (M.W. 492.17)

|  | C (%) | H (%) | N (%) | Cl (%) |
| --- | --- | --- | --- | --- |
| Calculated | 43.93 | 2.87 | 11.38 | 28.82 |
| Found | 43.61 | 2.88 | 11.03 | 28.90 |

The NMR spectrum shows δ values of 5.34 and 5.64 ppm for the CH₂ proton displacement as contrasted with 5.08 and 5.35 ppm for the other isomer. This finding allows one to identify the obtained product as the (Z) isomer, as this isomer can be expected to have the greater proton displacements.

EXAMPLE 3

(Z)-1-(4-Chlorophenyl)-2-(1H-imidazol-1-yl)-ethanone oxime

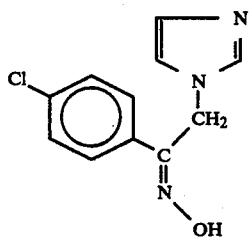

89.2 g 4-chlorophenacyl bromide is dissolved in 170 ml chloroform (or methylene chloride) and the solution is then added dropwise to a solution of 156 g imidazole in 600 ml chloroform (or methylene chloride, as the case may be) while maintaining the reaction mixture at about 0° to 5° C. Thereafter the mixture is continually stirred at this temperature for 4 hours, the solvent is distilled off in a rotation evaporator and the residue is treated with water. After filtering off and drying the precipitate and recrystallizing it in toluene one obtains 65 g p-chlorophenacyl imidazole or 1-(4-chlorophenyl)-2-(1H-imidazol-1-yl)-1-ethanone in the form of colorless crystals having a melting point of 158° to 160° C.

11 g (0.05 mol) of the p-chlorophenacyl imidazole thus obtained are dissolved in 110 ml ethanol together with 5.2 g (0.075 mol) hydroxylammonium chloride. 10 g (0.25 mol) solid sodium hydroxide are added to this solution with stirring. Thereafter the mixture is heated at its boiling point for one hour under reflux. Then after cooling the reaction mixture is poured into 175 ml aqueous 1n HCl, whereby the oxime is precipitated. The raw product which is obtained in this manner in an almost quantitative yield is recrystallized from ethanol. Thus Z-1-(4-chlorophenyl)-2-(1H-imidazol-1-yl)-ethanone oxime is obtaaied in the form of colorless crystals having a melting point of 194° to 195° C.

Elemental analysis for $C_{11}H_{10}ClN_3O$ (M.W. 235.7)

|  | C (%) | H (%) | N (%) | Cl (%) |
| --- | --- | --- | --- | --- |
| Calculated | 56.06 | 4.28 | 17.83 | 15.04 |
| Found | 56.22 | 4.31 | 17.45 | 15.12 |

EXAMPLE 4

(Z)-1-(4-Chlorophenyl)-2-(1H-imidazol-1-yl)-O-(4-chlorobenzyl)-ethanone oxime nitrate

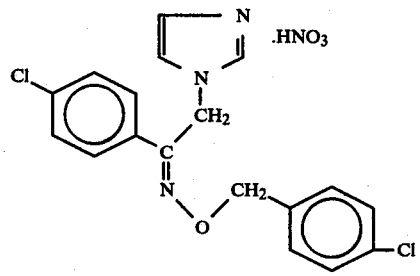

The procedure described in Example 2 is repeated except that the oxime of Example 3 is used and instead of 2,4-dichlorobenzyl chloride the equivalent amount of p-chlorobenzyl chloride is used.

After precipitation with aqueous nitric acid and recrystallization from ethanol the pure final product is obtained in the form of colourless crystals having a melting point of 161° C.

EXAMPLE 5

E-1-(4-Chlorophenyl)-2-(1H-imidazol-1-yl)-ethanone oxime

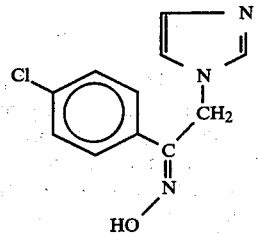

23.4 g (0.1 mol) p-chlorophenacyl bromide is dissolved in 300 ml methanol and 20.9 g (0.3 mol) hydroxylammonium chloride is added. Thereafter the mixture is briefly stirred and allowed to stand for about 14 to 16 hours at room temperature. The mixture is then diluted with water, whereby the reaction product is precipitated. The precipitate is filtered off, washed with water and dried.

20 g of a fairly pure raw product are obtained, which is subsequently recrystallized from "benzin" i.e., petroleum ether, (that is, a narrow-boiling-range hydrocarbon fraction with boiling points within the range of from between about 90° to 205° C.) The obtained Z-1-(4-chlorophenyl)-2-bromoethanone oxime forms colorless crystals having a melting point of 106° C.

5 g (0.02 mol) of the obtained halogen-Z-oxime are introduced with constant stirring into a previously prepared solution of 4 g (0.06 mol) imidazole in 40 ml chloroform. In this step the reaction temperature is maintained within the range between 0° and 5° C. by means of an ice bath. Upon completion of the addition the mixture is stirred for 3 more hours. The resulting precipitate is then filtered off and washed with water. 3 g of raw product are thus obtained and then recrystallized from ethanol. The stereochemically pure E-1-(4-chlorophenyl)-2-(1H-imidazol-1-yl)-ethanone oxime thus obtained forms colorless crystals having a melting point of 185° to 186° C.

Elemental analysis for $C_{11}H_{10}ClN_3O$ (M.W. 235.7)

|  | C (%) | H (%) | N (%) | Cl (%) |
| --- | --- | --- | --- | --- |
| Calculated | 56.06 | 4.28 | 17.83 | 15.04 |
| Found | 56.21 | 4.30 | 17.22 | 15.18 |

EXAMPLE 6

(E)-1-(2,4-Dichlorophenyl)-2-(1H-imidazol-1-yl)ethanone oxime (m.p. 205°–206° C.) is prepared from 2,4-dichlorophenacyl bromide using the procedure described in Example 5.

EXAMPLE 7

(E)-1-(2,4-Dichlorophenyl)-2-(1H-imidazol-1-yl)-O-(2,4-dichlorobenzyl)ethanone oxime nitrate

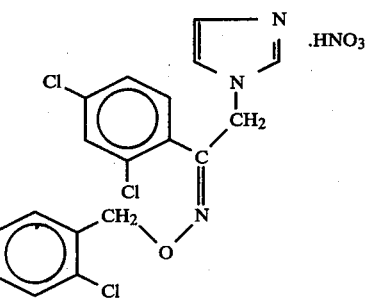

27 g (0.1 moles) (E)-1-(2,4-dichlorphenyl)-2-(1H-imidazol-1-yl)ethanone oxime (Example 6) is dissolved in 100 ml dimethylformamide (DMF). 2.16 g (0.09 moles) NaH is added to the solution and agitated for one hour at room temperature. Thereafter 20 g (>0.1 mol) 2,4-dichlorobenzyl chloride in 100 ml DMF are added to the mixture dropwise with agitation. After one hour the solvent is removed by means of a rotation evaporator. The residue is mixed with water and caused to crystallize by addition of aqueous 2n $HNO_3$. The raw nitrate thus obtained is recrystallized from ethanol after being separated by filtration and dried. A purified product is thus obtained in the form of colorless crystals weighing 10.5 g and having a melting point of 164° to 165° C.

Elemental analysis for $C_{18}H_{13}Cl_4N_3O \cdot HNO_3$ (M.W. 492.17)

|  | C (%) | H (%) | N (%) | Cl (%) |
| --- | --- | --- | --- | --- |
| Calculated | 43.93 | 2.87 | 11.38 | 28.82 |
| Found | 43.82 | 2.79 | 10.99 | 28.90 |

In the NMR spectrum δ values of 5.08 and 5.35 ppm are observed for the $CH_2$ protons. The values are smaller than the displacement values found for the other isomer and therefore justify identifying the isomer prepared in this Example 7 as the (E) form.

EXAMPLE 8

(E)-1-(4-Chlorophenyl)-2-(1H-imidazol-1-yl)-O-(4-chlorobenzyl)ethanone oxime nitrate

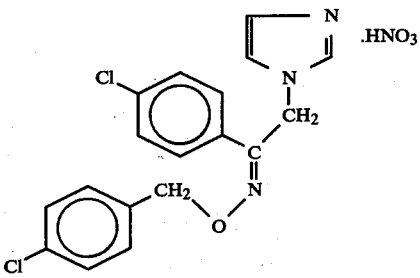

The procedure described in Example 7 is repeated except that the oxime of Example 5 is used and instead of 2,4-dichlorobenzyl chloride the equivalent amount of p-chlorobenzyl chloride is added.

The colourless crystalline reaction product has a melting point of 172° C. after recrystallization from ethanol.

EXAMPLE 9

(Z)-1-(2,4-Dichlorophenyl)-2-(1H-imidazol-1-yl)-O-benzyl-ethanone oxime nitrate (m.p. 130°–132° C.) is prepared using the procedure described in Example 2 above, except that benzyl chloride is substituted for 2,4-dichlorobenzyl chloride in the process.

It should be understood, of course, that the foregoing description and examples have been presented for purposes of illustration only and that many variations and modifications thereof are possible without departing from the scope of the claimed invention by using as reactants other compounds of the respective classes of compounds described.

For instance, in addition to the phenacyl bromides and chlorides specifically disclosed in the above examples, it is similarly convenient to use acyl chlorides or bromides wherein the radical A is an unsubstituted phenyl or naphthyl, e.g., phenacyl chloride or naphthacyl bromide, or other halo substituted derivatives such as 4-bromophenacyl chloride, 2,4-dibromophenacyl bromide, 4-fluorophenacyl bromide or 4-iodophenacyl chloride.

Likewise, by way of illustration, oximes that are particularly well suited for use in this invention include imidazole oximes of formula (II) wherein Im is an unsubstituted imidazolyl group and A represents 4-bromophenyl, 2,4-dibromophenyl, 4-fluorophenyl or 4-iodophenyl.

In the case of the ether forming compounds corresponding to formula (III), representative species that are especially convenient to use include, for instance, organic chlorides or bromides or sulfonic acid esters wherein the radical B is a $C_1$ to $C_4$ alkyl, allyl, methylphenyl or ethylphenyl, methylthienyl, ethylthienyl, benzyl, phenoxymethyl, phenoxybutyl, pyridyl, phenethyl or pyranylmethyl.

The scope of the invention for which patent protection is sought is particularly pointed out in the appended claims.

We claim:

1. A process for the stereospecific production of a substantially pure imidazolyl oxime stereoisomer having the formula

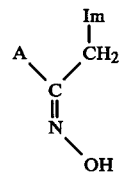

wherein

A signifies a phenyl with from zero to two halogeno substituents, and

Im signifies a 1-H-imidazol-1-yl group that is substituted with zero to two substituents selected from the class consisting of halogeno and $C_1$–$C_4$ alkyl which process comprises:

(a) first reacting a 2-halogen ethanone of the formula

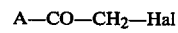

wherein Hal is a halogen and A has the meaning given above, with imidazole or a substituted imidazole containing the substituents as given above for Im thereby forming the corresponding 2-(imidazol-1-yl) derivative of the halogen ethanone (IV), (b) then heating said imidazolyl derivative in alcoholic solution with hydroxylamine or a hydroxylamine-yielding compound in the presence of an amount of an alkali corresponding to a molar excess relative to said hydroxylamine and hydroxylamine-yielding compound, respectively, to produce a substantially pure cis-oxime stereoisomer of formula ($II_c$), and (c) recovering said cis-oxime stereoisomer.

* * * * *